(12) United States Patent
Haber et al.

(10) Patent No.: US 12,419,579 B2
(45) Date of Patent: Sep. 23, 2025

(54) METHOD, SYSTEM AND DEVICE FOR NONINVASIVE CORE BODY TEMPERATURE MONITORING

(71) Applicants: Mordehy Haber, Tel Aviv (IL); Simi Haber, Ramat Gan (IL); Benny Pesach, Rosh Ha'ayin (IL)

(72) Inventors: Mordehy Haber, Tel Aviv (IL); Simi Haber, Ramat Gan (IL); Benny Pesach, Rosh Ha'ayin (IL)

( * ) Notice: Subject to any disclaimer, the term of this patent is extended or adjusted under 35 U.S.C. 154(b) by 4 days.

(21) Appl. No.: 17/857,728

(22) Filed: Jul. 5, 2022

(65) Prior Publication Data

US 2022/0338811 A1    Oct. 27, 2022

Related U.S. Application Data

(63) Continuation of application No. 16/489,935, filed as application No. PCT/IL2018/000002 on Mar. 13, 2018, now Pat. No. 11,406,326.

(60) Provisional application No. 62/471,070, filed on Mar. 14, 2017.

(51) Int. Cl.
| | |
|---|---|
| *A61B 5/01* | (2006.01) |
| *A61B 5/00* | (2006.01) |
| *G01K 1/16* | (2006.01) |
| *G01K 7/42* | (2006.01) |
| *G01K 13/20* | (2021.01) |
| *G01K 15/00* | (2006.01) |

(52) U.S. Cl.
CPC .............. *A61B 5/6844* (2013.01); *A61B 5/01* (2013.01); *G01K 1/165* (2013.01); *G01K 7/427* (2013.01); *G01K 13/20* (2021.01); *G01K 15/005* (2013.01); *A61B 2560/0223* (2013.01)

(58) Field of Classification Search
CPC . A61B 5/6844; A61B 5/01; A61B 2560/0223; G01K 15/005
See application file for complete search history.

(56) References Cited

U.S. PATENT DOCUMENTS

| | | | |
|---|---|---|---|
| 2015/0290065 A1* | 10/2015 | Augustine | ................ A61G 7/05 5/655.3 |
| 2016/0038036 A1* | 2/2016 | Augustine | .............. G01K 1/165 600/549 |

* cited by examiner

*Primary Examiner* — Daniel L Cerioni

(57) ABSTRACT

A core body temperature monitoring apparatus placed superdermally over a user's skin, including a first temperature sensor, a second temperature sensor, a thermal insulation layer positioned intermediate the first and second temperature sensor and a heater for heating the apparatus and a subdermal tissue region underlying the user's skin. The subdermal tissue region is configured with variable thermal tissue parameters. A controller includes a switch configured for alternating between a calibration mode, wherein the heater is activated for calculating an instantaneous thermal tissue parameter, and a measurement mode, wherein the heater is inactive and the core body temperature is determined, based on the calculated instantaneous thermal tissue parameter.

12 Claims, 9 Drawing Sheets

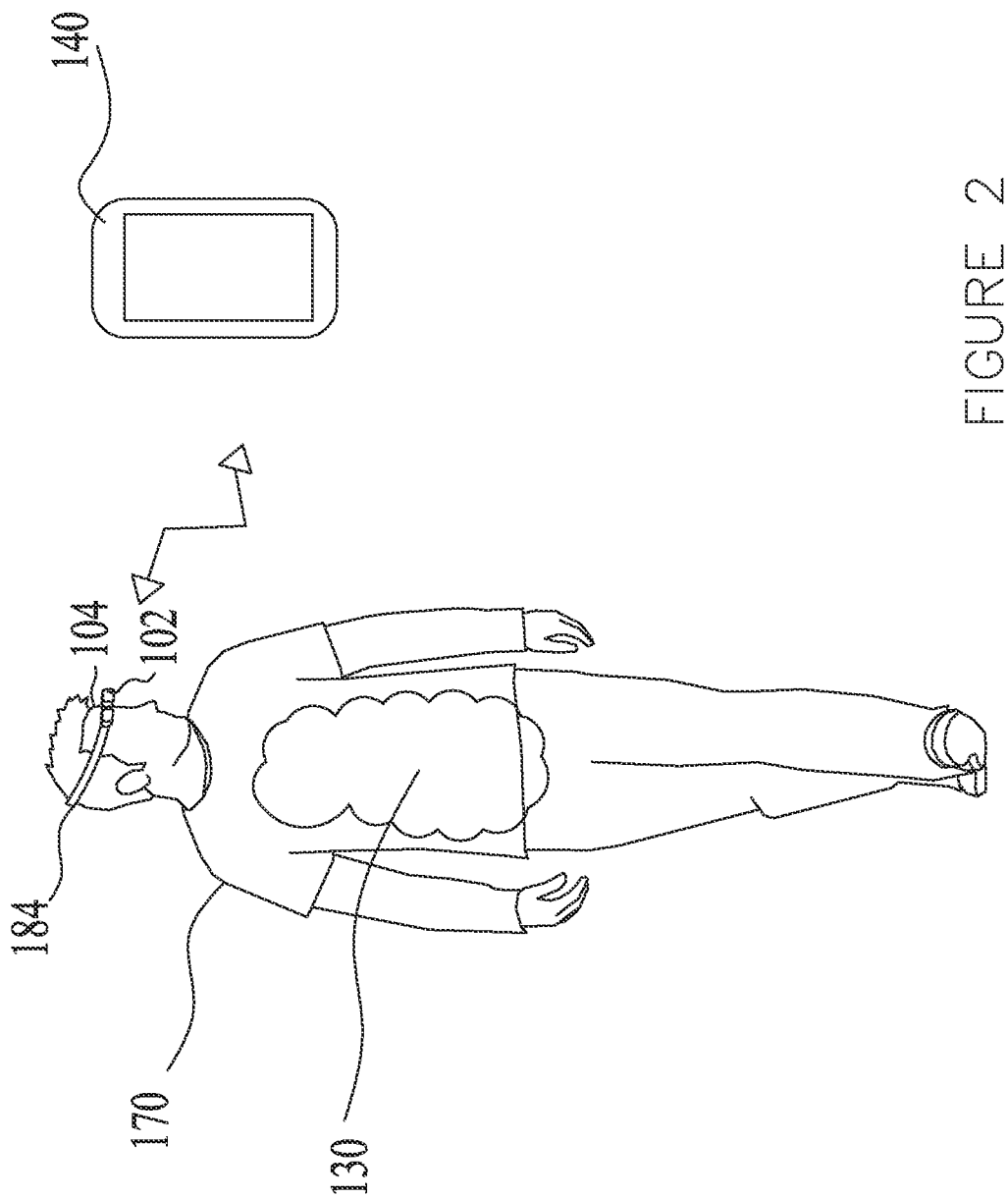

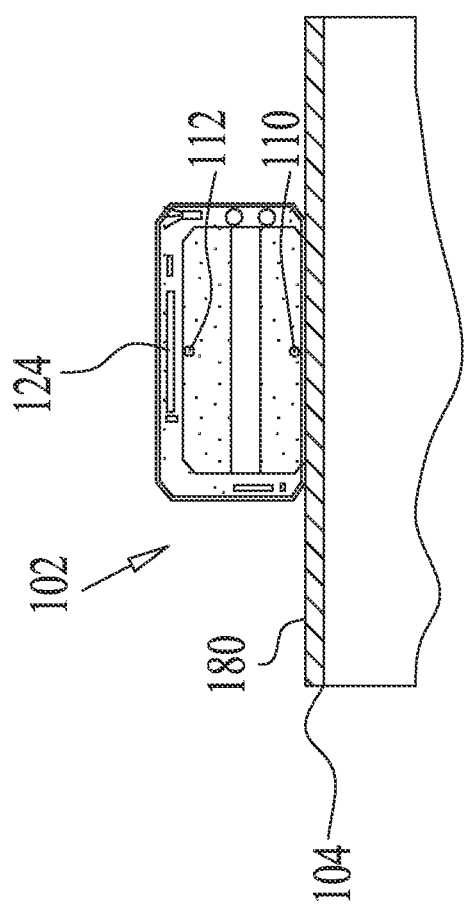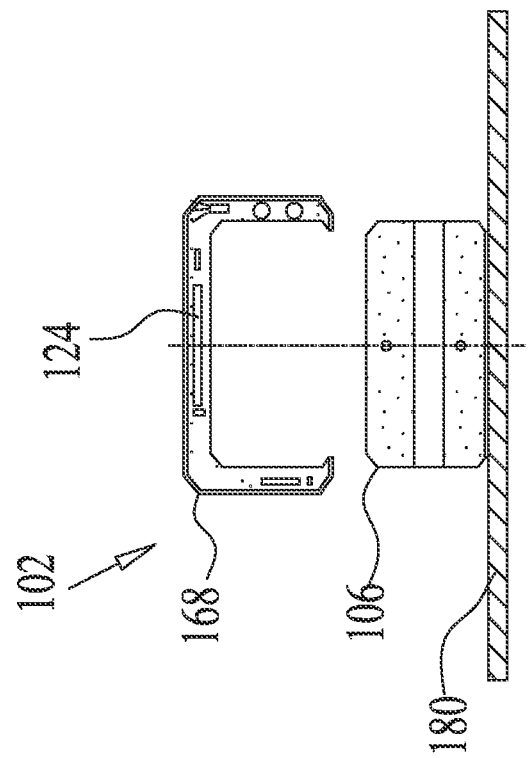

METHOD, SYSTEM AND DEVICE FOR NONINVASIVE CORE BODY TEMPERATURE MONITORING

CROSS-REFERENCE TO RELATED APPLICATIONS

This application is a continuation of U.S. patent application Ser. No. 16/489,935, filed on Aug. 29, 2019, which claims the benefit of International Patent Application No. PCT/IL2018/000002, filed Mar. 13, 2018 and entitled "Method, System and Device for Noninvasive Core Body Temperature Monitoring" which claims priority to U.S. Provisional Patent Application No. 62/471,070, filed Mar. 14, 2017. The present application incorporates herein by reference the disclosures of each of the above-referenced application in their entireties.

TECHNICAL FIELD

Some embodiments of the present disclosure generally relate to methods, systems and devices for monitoring a core body temperature.

BACKGROUND

Human body temperature is a vital signal of importance in many medical circumstances. The human body regulates the temperature of its inner organs, namely the core body temperature (CBT), maintaining the core body temperature around a set point of homeostasis.

Large deviations from this point, such as during hypothermia and hyperthermia, are dangerous and may be fatal if untreated. Superficial skin temperature is an insufficient indicator of core body temperature in many cases, such as in sedated patients or in extreme environments as well as in normal conditions. Currently, rectal measurements are considered the standard for core body temperature measurement. Monitoring is usually performed using a catheter or by invasive means.

Heat flow based techniques have been used for the development of noninvasive core body temperature sensors. These sensors offer a solution for situations where invasive methods are shunned, such as for lightly or locally sedated patients in hospitals. However these sensors have many limitations, such as having relatively high energy consumption, having limited accuracy, being dependent on environmental conditions, and on the measured organ. These drawbacks hinder these sensors applicability to most out-of-hospital applications.

Therefore, there is a need for noninvasive apparatuses with low power consumption and accurate monitoring of core body temperature, which may be applicable for outdoor environments.

SUMMARY OF SOME EMBODIMENTS

The following summary of the invention is included in order to provide a basic understanding of some aspects and features of the disclosure. This summary is not an extensive overview of the disclosure and as such it is not intended to particularly identify key or critical elements of the disclosure or to delineate the scope of the disclosure. Its sole purpose is to present some concepts of the disclosure in a simplified form as a prelude to the more detailed description that is presented below.

There is provided according to some embodiments of the present disclosure a temperature monitoring system configured for determining the core body temperature. The core body temperature monitoring system may comprise a noninvasive temperature monitoring apparatus, generally positioned superdermally. The temperature monitoring apparatus may comprise at least a pair of a first temperature sensor and a second temperature sensor separated by a predetermined medium, such as a thermal insulation layer. The first temperature sensor is configured for detecting the temperature, denoted by $T_1$. The first temperature sensor may be positioned below the insulation layer, generally in proximity to the epidermis surface. The second temperature sensor is configured for detecting the temperature, denoted by $T_2$, above the thermal insulation layer. The thermal insulation layer is formed with a predetermined thermal conductivity constant, denoted by $C_1$.

Deriving from Heat Flux formulations, a bodily subdermal tissue temperature, denoted by $T_0$ may be determined based on the temperature gradient between $T_1$ and $T_2$ and physical properties of the predetermined medium and the physical properties of the subdermal tissue.

In some embodiments, the physical property of the predetermined medium may comprise the thermal conductivity constant $C_1$ and the physical property of the subdermal tissue may comprise the subdermal tissue thermal conductivity constant, denoted by $C_t$.

Yet $C_t$ may vary amongst different individuals and may be affected by a plurality of factors, such as environmental changes or physical changes. This variable parameter, $C_t$, may be determined by initially activating a calibration mode for calculating the instantaneous $C_t$.

A controller switches the system to a measurement mode to calculate the body subdermal tissue temperature, $T_0$, thereby determining the core body temperature.

The controller is further configured to alternate between the measurement mode and to the calibration mode, whereupon there is a requirement for recalibration of $C_t$, thereby providing a superiorly accurate core body temperature measurement.

The temperature monitoring apparatus may be configured with relatively minimal power consumption due to relying on passive components or elements for operating the measurement mode and minimal use of active components generally only during the calibration mode. The low power consumption allows the temperature monitoring apparatus to be portable and used outdoors for a prolonged duration.

There is thus provided according to some embodiments, a core body temperature monitoring apparatus placed superdermally over a user's skin, including a first temperature sensor, a second temperature sensor, a thermal insulation layer positioned intermediate the first and second temperature sensor, a heater for heating the apparatus and a subdermal tissue region underlying the user's skin. The subdermal tissue region is configured with variable thermal tissue parameters. A controller includes a switch configured for alternating between a calibration mode, wherein the heater is activated for calculating an instantaneous thermal tissue parameter of the variable thermal tissue parameters, and a measurement mode, wherein the heater is inactive and the core body temperature is determined, based on the calculated instantaneous thermal tissue parameter.

In some embodiments, the apparatus further includes a communication port for transmitting the determined core body temperature to an external device. The communication between the apparatus and the external device may be via the Cloud.

In some embodiments, the apparatus may further include a power source for supplying power to the heater. In some embodiments, the power source is a battery. In some embodiments, the battery has a capacity in the range of at least 500-10,000 milliampere-hour (mAh) being configured to allow the apparatus to be used remotely, away from an electrical grid.

In some embodiments, the apparatus determines the core body temperature by being placed non-invasively, over a user's skin.

In some embodiments, more than one core body temperature monitoring apparatus is provided such that wherein a first core body temperature monitoring apparatus operates in a calibration mode, a second core body temperature monitoring apparatus operates in a measurement mode.

In some embodiments, the first temperature sensor, the second temperature sensor, the thermal insulation layer, and the heater are disposable and the controller is reusable.

The apparatus may be designed to measure a local dermal blood flow.

In some embodiments, the heater is positioned at least at one of the following positions: intermediate the first temperature sensor and the second temperature sensor, below the first temperature sensor and above the second temperature sensor. The apparatus may include a plurality of heaters. The apparatus may include a plurality of temperature sensors.

In some embodiments, the apparatus may further including a housing and a peripheral thermal insulation layer. The controller and the switch may be embedded in a CPU.

In some embodiments, the apparatus is attached to a band. In some embodiments, a heart rate monitor is provided to verify physical coupling of apparatus to the user's epidermis surface.

In some embodiments, the apparatus further includes at least one of an environmental sensor and a bodily function sensor.

There is further provided according to some embodiments, a core body temperature monitoring apparatus placed superdermally over a user's skin, including a first temperature sensor, a second temperature sensor, a thermal insulation layer positioned intermediate the first and second temperature sensor, a heater, and a controller including a switch for alternating between an active mode, wherein the heater is activated, and a passive mode, wherein the heater is inactive and wherein the core body temperature is determined.

There is yet provided according to some embodiments, a core body temperature monitoring apparatus placed superdermally over a user's skin, including a first temperature sensor, a second temperature sensor, a thermal insulation layer positioned intermediate the first and second temperature sensor, a heater for heating the apparatus and a subdermal tissue region underlying the user's skin. The subdermal tissue region is configured with variable thermal tissue parameters. A controller includes a switch, the switch is configured for alternating between a calibration mode, wherein the heater is activated for calculating an instantaneous thermal tissue parameter, and a measurement mode, wherein the heater is inactive and the core body temperature is determined, based on the calculated instantaneous thermal tissue parameter. The controller has operating thereon processor instructions for causing the switch to alternate between the calibration mode and the measurement mode based on at least one of a predetermined duration from a previous core body measurement, a change in an environmental condition, and a change in a physical condition of the user.

There is moreover provided according to some embodiments, a multiple core body temperature monitoring apparatus including at least a first and second core body temperature monitoring apparatus placed superdermally over a user's skin, wherein each apparatus includes a first temperature sensor, a second temperature sensor, a thermal insulation layer positioned intermediate the first and second temperature sensor, and a heater for heating the apparatus and a subdermal tissue region underlying the user's skin. The subdermal tissue region is configured with variable thermal tissue parameters. A controller includes a switch. The switch is configured for alternating between a calibration mode, wherein the heater is activated for calculating an instantaneous thermal tissue parameter, and a measurement mode, wherein the heater is inactive and the core body temperature is determined, based on the calculated instantaneous thermal tissue parameter, the controller is common for the at least a first and second core body temperature monitoring apparatus.

In some embodiments, the apparatus includes a housing common for at least the first and second core body temperature monitoring apparatus.

There is thus provided according to some embodiments, a temperature monitoring apparatus placed superdermally over a user's skin, including a thermal insulation layer positioned intermediate a first and second temperature sensor, a heater for heating the apparatus and a subdermal tissue region underlying the user's skin. The subdermal tissue region is configured with variable thermal tissue parameters, the first temperature sensor is located between the thermal isolation layer and user's skin, the second temperature sensor is located on the other side of the thermal isolation layer, and a controller that receives signals from the first and second temperature sensors and controls the heater according to at least two modes that temporally switch between a calibration mode, wherein the heater is activated for calculating an instantaneous thermal tissue parameter of the variable thermal tissue parameter, and a measurement mode, wherein the heater is inactive and the core body temperature is determined, based on the calculated instantaneous thermal tissue parameter.

There is thus provided according to some embodiments, a core body temperature monitoring apparatus placed superdermally over a user's skin, comprising passive elements, an active element and a controller comprising a switch. The switch is configured for alternating between an active mode wherein the active element is activated for calculating an instantaneous thermal tissue parameter; and a passive mode, wherein the active element is terminated and the core body temperature is determined, based on signals received by the passive elements and the calculated instantaneous thermal tissue parameter. The passive elements may comprise a first temperature sensor, a second temperature sensor, a thermal insulation layer positioned intermediate the first and second temperature sensors. The active element may comprise a heater for heating the apparatus and a subdermal tissue region underlying the user's skin.

There is thus provided according to some embodiments, a method for determining a core body temperature, including initially activating a calibration mode including heating a temperature monitoring apparatus for calculating an instantaneous thermal tissue parameter, the apparatus includes a first temperature sensor, a second temperature sensor, and a thermal insulation layer positioned intermediate the first and second temperature sensor, the apparatus being positioned superdermally over a user's skin, the heating is activated until temperature equilibrium is achieved between the first temperature sensor and the second temperature sensor, activating a measurement mode, wherein the heating is terminated and the core body temperature is determined, based on the calculated instantaneous thermal tissue parameter.

In some embodiments, the method further includes verifying coupling of the temperature monitoring apparatus to the superdermal surface. In some embodiments, a rate of blood perfusion is detected by the amount of time it takes for temperature of the first or second temperature sensor to return to its initial temperature following heating.

In some embodiments, the activation of the calibration mode and the measurement mode is performed by a controller including a switch operative to alternate between the calibration mode and the measurement mode. In some embodiments, the switch is configured to alternate between the calibration mode and the measurement mode based on a predetermined trigger.

In some embodiments, the trigger includes passage of a predetermined duration. In some embodiments, the trigger includes an environmental change or a physical change.

There is yet provided according to some embodiments, a method for determining a core body temperature, including activating a calibration mode to determine a thermal conductivity constant of a subdermal tissue, $C_t$, including heating a temperature monitoring apparatus until temperature equilibrium is achieved, the temperature sensor subassembly including a first temperature sensor measuring a temperature $T_1$, a second temperature sensor measuring a temperature $T_2$, and a thermal insulation layer positioned intermediate the first and second temperature sensor and designed with a thermal conductivity constant $C_1$, the apparatus being positioned superdermally over a user's skin, the heating being activated until temperature equilibrium is achieved between the first temperature sensor and the second temperature sensor, measuring the temperature of the first or second temperature sensor to establish a subskin tissue temperature, $T_{0t}$. Terminating the heating and thereby calculating the thermal conductivity constant of the subdermal tissue, $C_t$ according to $$Ct = \frac{(T1 - T2)C1}{T0t - T1}.$$

Activating a measurement mode, wherein the core body temperature is determined, based on the calculated thermal conductivity constant Ct, determining the core body temperature, $T_{0\ CBT}$ based on $$T_{0CBT} = T_1 + \frac{(T1 - T2)}{Ct}$$

BRIEF DESCRIPTION OF THE DRAWINGS

The principles and operations of the systems, apparatuses and methods according to some embodiments of the present disclosure may be better understood with reference to the drawings, and the following description. The drawings are given for illustrative purposes only and are not meant to be limiting.

FIG. 2 is a simplified, exemplary illustration of a temperature monitoring system constructed and operative according to some embodiments of the present disclosure;

FIGS. 3A and 3B are respective assembled and disassembled simplified, exemplary illustrations of a temperature monitoring apparatus, constructed and operative according to some embodiments of the present disclosure;

DETAILED DESCRIPTION OF SOME OF THE EMBODIMENTS

In the following description, various aspects of the present invention will be described with reference to different embodiments. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

Figures 1A, 1B:
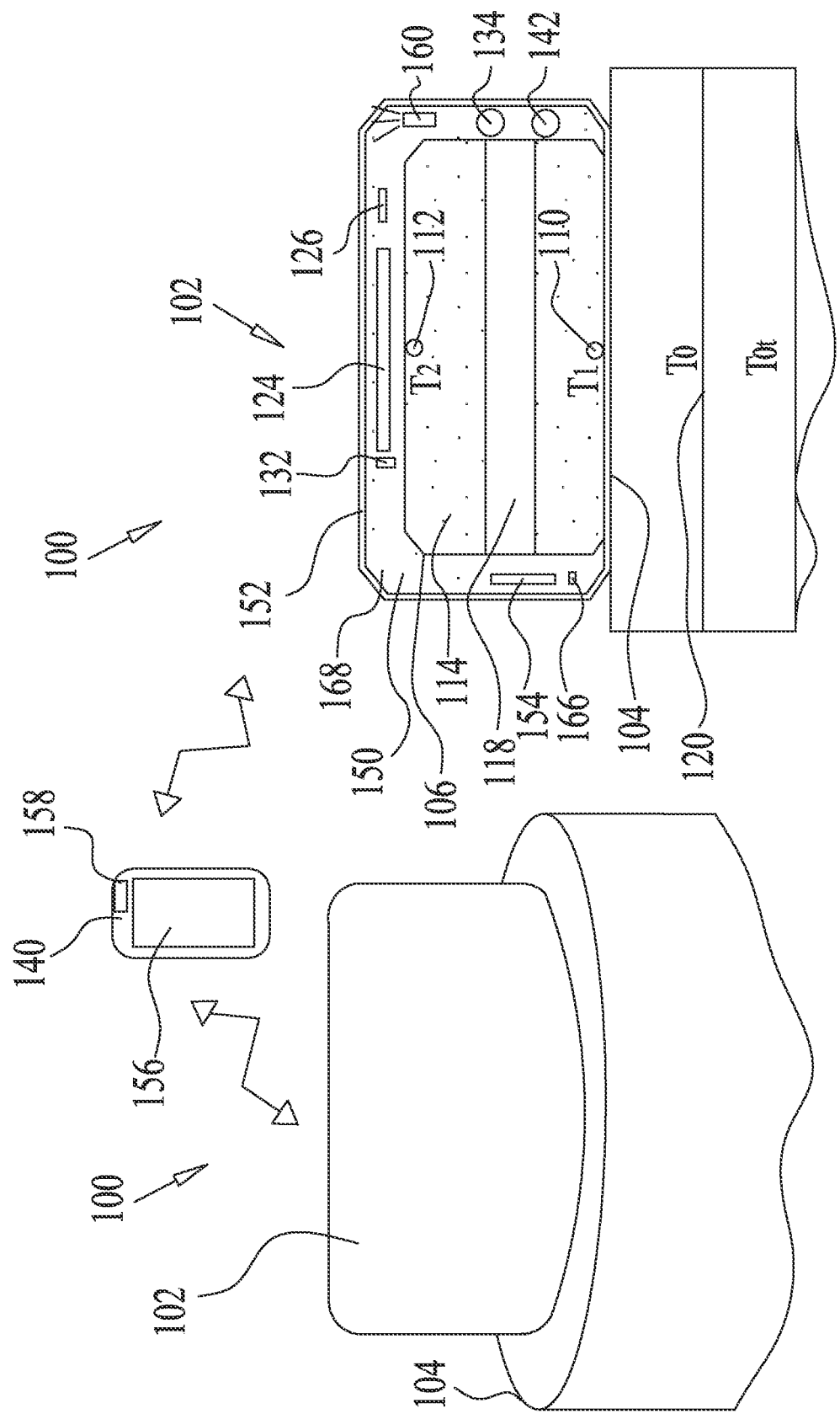
FIGS. 1A and 1B are a simplified, exemplary illustration of a temperature monitoring system (FIG. 1A) and a cross sectional view thereof (FIG. 1B), constructed and operative according to some embodiments of the present disclosure.

FIGS. 1A, 1B and 2 are a simplified, exemplary illustration of a temperature monitoring system 100, constructed and operative according to some embodiments of the present disclosure. The temperature monitoring system 100 is configured for determining the core body temperature (CBT). In some embodiments the system 100 may comprise a non-invasive temperature monitoring apparatus 102 positioned superdermally above the epidermal surface 104.

The temperature monitoring apparatus 102 may comprise a temperature sensor subassembly 106 comprising at least a pair of a first temperature sensor 110 and a second temperature sensor 112 separated by a predetermined medium, such as an intermediate thermal insulation layer 114 or any thermal insulation/isolation medium. The first and second temperature sensors 110 and 112 are provided for measuring the heat flow from the epidermal surface 104. The first temperature sensor 110 is configured for detecting the temperature in proximity to the epidermis, denoted by $T_1$ and second temperature sensor 112 is configured for detecting the temperature above the thermal insulation layer 114, denoted by $T_2$. The insulation layer 114 may be formed of any suitable material. The thermal insulation layer 114 is formed with a predetermined thermal conductivity constant, denoted by $C_1$.

Deriving from Heat Flux formulations, a bodily subdermal/tissue temperature, denoted by To, may be determined based on $T_1$, $T_2$, (of the first and seconds sensors 110 and 112) the thermal conductivity constant of the insulation layer 114, $C_1$, and a variable thermal tissue parameter, (e.g. by Equation (1)).

The bodily subdermal temperature To, measures the temperature at the subdermal tissue region, which is the tissue region underlying the user's skin, namely underlying the epidermal surface 104. The subdermal tissue region is configured with the variable thermal tissue parameter.

In some embodiments, the thermal tissue parameter may comprise the tissue thermal capacitance. In some embodiments, the thermal tissue parameter may comprise the tissue thermal resistance, and/or a level of the tissue heat transfer properties, such as convection or radiation.

In some embodiments, the thermal tissue parameter may comprise the thermal conductivity constant of the subdermal tissue, denoted by $C_t$.

This in accordance with Equation (1) wherein:

$$To = T1 + \frac{(T1-T2)C1}{Ct} \qquad \text{Equation (1)}$$

The core body temperature (CBT) may be measured by proxy by calculating the bodily subdermal temperature $T_0$.

The $T_1$ and $T_2$ parameters are detected by first temperature sensor 110 and second temperature sensor 112. $C_1$ is predetermined and known in accordance with the properties of the insulating layer 114, and is assumed to remain static.

The $C_t$ parameter (the thermal conductivity constant of the subdermal tissue) may vary amongst different individuals. Furthermore, the $C_t$ parameter typically remains static until occurrence of an environmental change or physical change in the subdermal tissue, such as the flow of bodily fluids through the subdermal tissue, e.g. dermal blood perfusion, or rise in the environment temperature, causing $C_t$ to deviate. This variable parameter, $C_t$, may be determined by activating a calibration mode where initially zero heat flux (ZHF) is achieved by a heater 118 (or any heating element) during a ZHF phase. The heater 118 is activated to generate an isothermal channel, extending longitudinally through the temperature sensor subassembly 106 from the second temperature sensor 112 to the first temperature sensor 110 through to a subskin location 120. The heater 118, governed by a controller 124, may be configured to heat to a relatively slight degree for a relatively short time to prevent heating the subdermal tissue.

In a non limiting example, the heat may be generated by the heater 118 for 1 minute or less, for 2 minutes or less, for 3 minutes or less, for 5 minutes or less, for 10 minutes or less, for 20 minutes or less, for 30 minutes or less, including values and subranges therebetween. The controller 124 may activate the heater 118 to raise the temperature of the subskin location 120 by 1 degree ° C. or less, by 2 degrees ° C. or less, by 3 degrees ° C. or less, by 5 degrees ° C. or less, by 7 degrees ° C. or less, by 10 degrees ° C. or less, by 15 degrees ° C. or less, including values and subranges therebetween. The depth of subskin location 120 may be relatively small, such as about 5 millimeters under the epidermal surface 104 or less, or about 7 millimeters under the epidermal surface 104 or less, or about 9 millimeters under the epidermal surface 104 or less, or about 11 millimeters under the epidermal surface 104 or less, or about 13 millimeters under the epidermal surface 104 or less, or about 15 millimeters under the epidermal surface 104 or less, including values and subranges therebetween. In some embodiments, the subskin location 120 may be within the dermis layer, which typically has a depth spanning from 5-10 millimeters from the epidermal surface 104. In some embodiments, the subskin location 120 may be within the subcutaneous layer, which typically has a depth spanning from about 10 millimeters from the epidermal surface 104 and deeper to the body core region 130.

The body core region 130 is schematically illustrated, at least partially, in FIG. 2.

In a non-limiting example, the heat may be generated by the heater 118 for a predetermined duration and may decrementally decrease as the difference in the temperatures of $T_1$ and $T_2$ decreases. For example, at a first one second cycle the heat is generated for 0.9 seconds and is terminated for 0.1 seconds. At the following one second cycles the heat duration is decreased until the heat is generated for 0.1 seconds and is terminated for 0.9 seconds.

The isothermal channel is generated whereupon zero heat flux is achieved and $T_1$ equals $T_2$. In accordance with Equation 1, $T_0$, measured at the proximal subskin location 120, (denoted by $T_{0t}$) is equal to $T_1$ as well as $T_2$. Since $T_1$ is detectable by first temperature sensor 104, $T_{0t}$ is likewise known since $T_{0t}=T_1$. The subskin temperature $T_{0t}$, which is an instantaneous, calibration subdermal temperature, may be transmitted to the controller 124 and stored in a memory module 126.

Upon reaching zero heat flux, the controller 124 may terminate the heating, thereby commencing a heat flux (HF) phase by creating a heat flow channel, such that $T_1$ is larger or smaller than $T_2$, namely $T_1 \neq T_2$. The stored $T_{0t}$ may be retrieved from memory 126 so as to calculate the $C_t$, as derived from Equation 1, such that:

$$Ct = \frac{(T1-T2)C1}{T0t-T1}$$

The $C_t$ may be stored within memory 126. The effective $C_t$ parameter is relevant to both the dermis layers and subdermal tissues at location 120 and its vicinity, as well as the core body tissues at region 130. $C_t$ may be retrieved by the controller 124 for calculating the subdermal tissue temperature, $T_0$ during a measurement mode, thereby determining the core body temperature, $T_{0\,CBT}$ as:

$$T_{0CBT} = T_0 = T_1 + \frac{(T1-T2)C1}{Ct}$$

In some embodiments, the controller 124 may activate a switch 132 configured to alternate between the calibration mode and the measurement mode based on any suitable condition or trigger. In some embodiments, the switch 132 may be configured to alternate modes based on a predetermined duration of time from the activation of a previous measurement mode, or based on an environmental change or based on a physical change or any other trigger.

In some embodiments, temperature monitoring system 100 may comprise an environmental sensor 134 configured to detect changes in the ambient temperature or any other parameter, such as humidity, and/or sun radiation, for example. The environmental sensor 134 may be embedded within the temperature monitoring apparatus 102, as shown in FIG. 1B, or may be placed on the body or within an external device 140 or at any other suitable location within the temperature monitoring system 100.

In some embodiments, the temperature monitoring system 100 may comprise a bodily function sensor 142 configured to detect physical changes, such as skin temperature which may be measured by a temperature sensor; or cardiac activity, such as pulse, which may be measured by a pulse meter or an ECG (Electrocardiography) device for measuring the electrical activity of the heart, for example; or physical activity level, which may be measured by a pedometer, for example or by measurement of perspiration levels secreted by the user.

Other physical changes may comprise changes in a dermal blood perfusion rate which may be measured in any suitable manner, such as by an optical device. In some embodiments, the optical device may be designed to detect the color of the blood as an indicator of the degree of dermal blood perfusion. In some embodiments, the optical device may be designed to detect the hemoglobin wavelength as an indicator of the degree of dermal blood perfusion or interference measurement such as with an optical Doppler sensor. In some embodiments, the degree of dermal blood perfusion may be measured acoustically, such as by an ultrasonic flow meter or by a Doppler flow meter.

The bodily function sensor 142 may be embedded within the temperature monitoring apparatus 102, as shown in FIG. 1B, or may be placed on the body or within an external device 140 or at any other suitable location within the temperature monitoring system 100.

In some embodiments, the external device 140, e.g., a mobile phone, may wirelessly (or via a wired connection) transmit information related to the change conditions, such as the ambient temperature or humidity level, and/or sun radiation, which is an indication of the direct exposure to the sun. The sun radiation, as well as UV rays may be measured by any suitable radiation meters or UV meters, for example. Likewise the change conditions may include physical changes, such as the skin temperature, cardiac activity, physical activity, perspiration level and dermal blood perfusion, for example.

Figure 7:
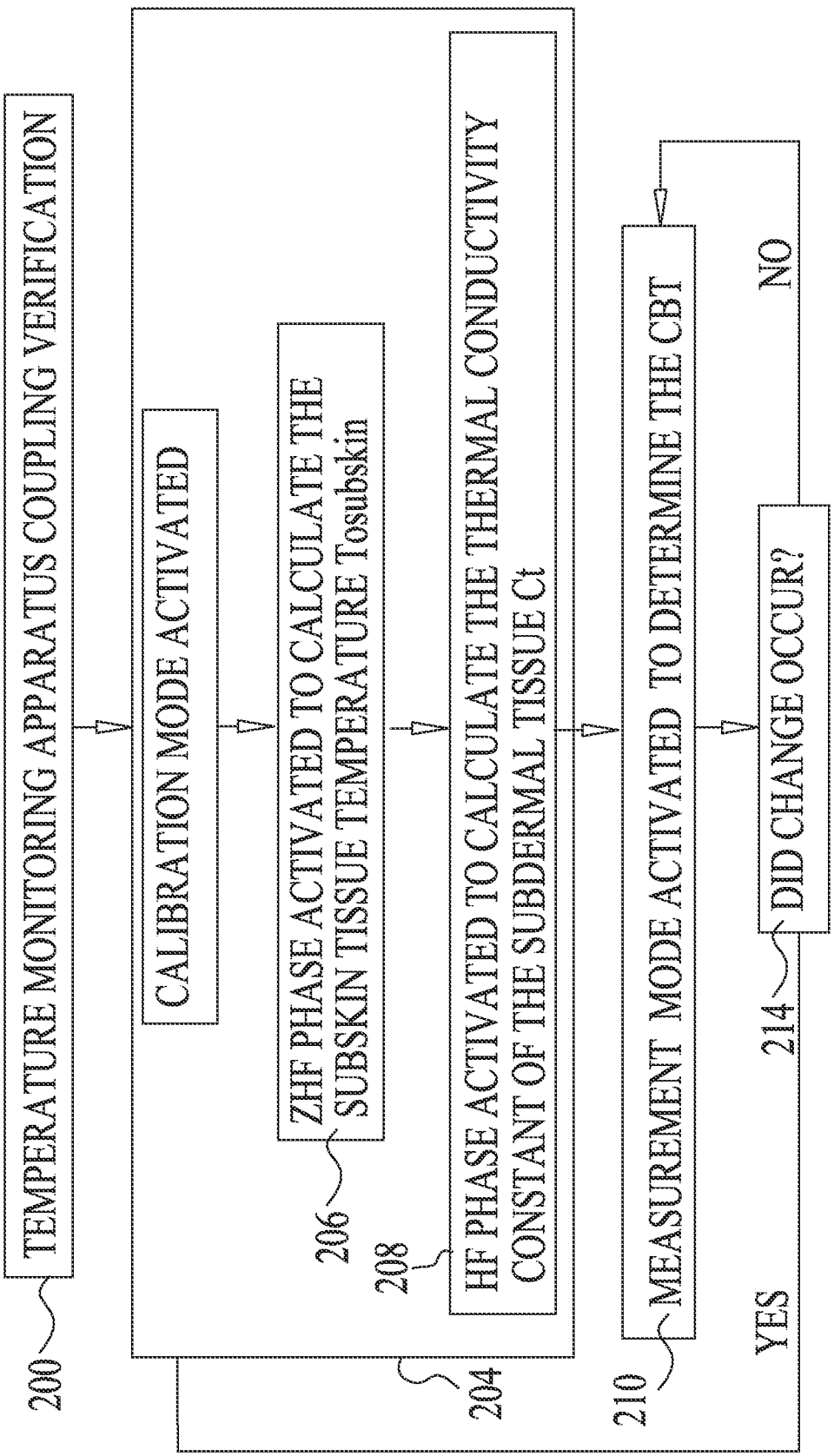
FIG. 7 is a simplified flowchart of a method for determining the core body temperature, constructed and operative according to some embodiments of the present disclosure.
Figure 8:
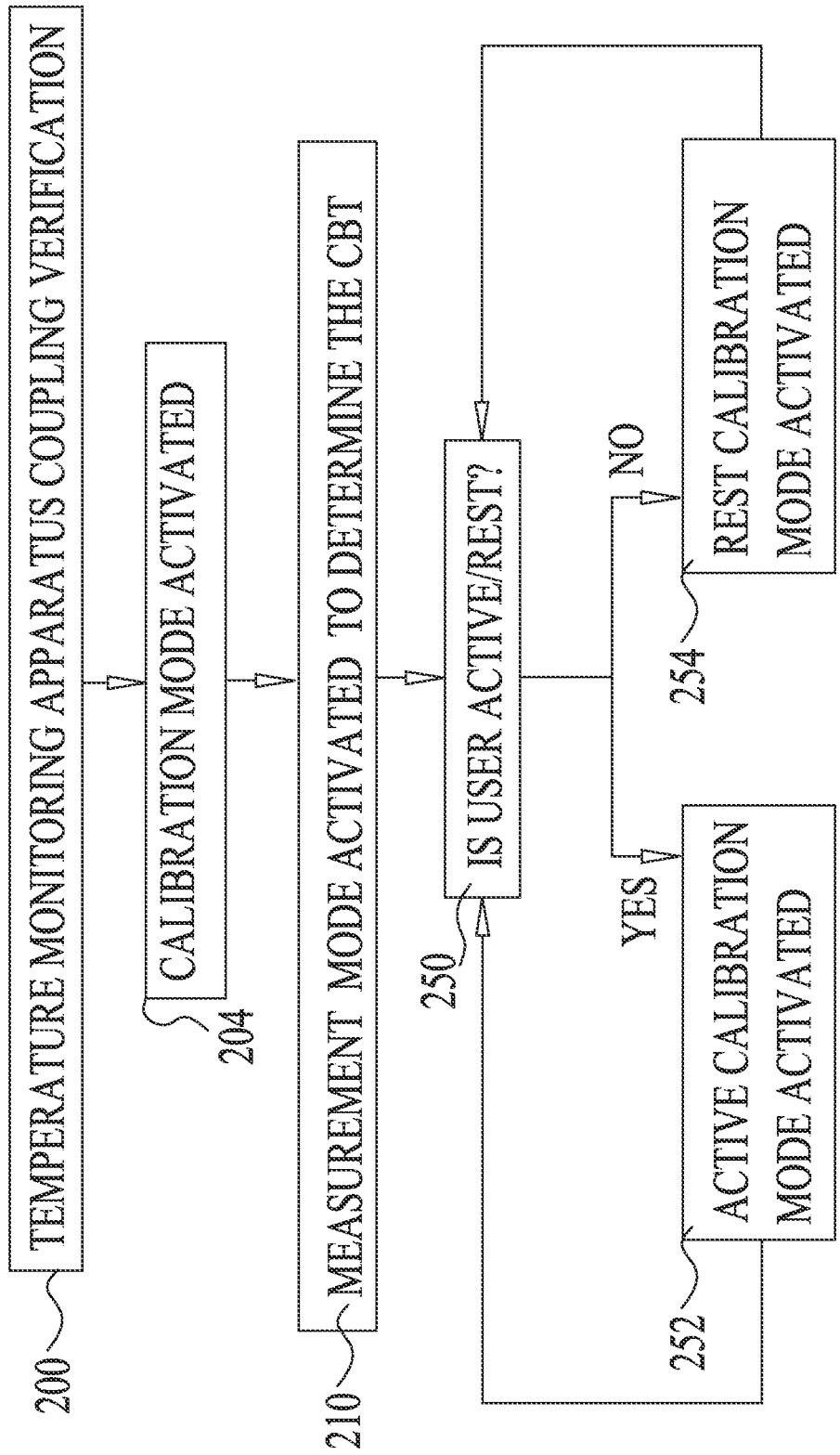
FIG. 8 is a simplified flowchart of a method for determining the core body temperature, constructed and operative according to some embodiments of the present disclosure.

Exemplary steps in operation of the temperature monitoring system 100 and performance of the switch 132 altering between the calibration mode and the measurement mode are shown in FIGS. 7 and 8.

In some embodiments, the temperature monitoring apparatus 102 may comprise a peripheral thermal insulation layer 150 encasing the temperature sensor subassembly 106 and underlying a housing 152.

The temperature monitoring apparatus 102 may be provided with a power supply source 154. In some embodiments, the power supply source 154 may include a rechargeable or disposable battery, a backup battery, a microgenerator, and/or a wired or wireless connection to electricity or another power source. In some embodiments, the power source 154 may be provided by the external device 140.

The power source 154 may be configured to be relatively small to properly fit within a wearable temperature monitoring apparatus 102, yet with sufficient power for prolonged, wireless use of the temperature monitoring apparatus 102 so as to allow the temperature monitoring apparatus 102 to be used in the outdoors. In a non-limiting example, the power source 154 may comprise a battery with a capacity of at least 500 milliampere-hour (mAh) or more, or at least 1000 mAh or more, or at least 2000 mAh, or at least 3000 mAh, or at least 4000 mAh or more, or at least 5000 mAh or more, or at least 10,000 mAh or more, including values and subranges. The battery capacity may be sufficient for at least a few hours, or at least a day, or at least a few days or weeks, prior to recharging the battery.

The determined core body temperature may be transmitted from the temperature monitoring apparatus 102 to the external device 140 for storage and further analysis thereof.

In some embodiments, the external device 140 may comprise a mobile device, such as a mobile phone. In some embodiments, the external device 140 may be any type of device having computing capabilities, such as, but not limited to, a personal computer, a cellular phone, a smartphone, a tablet, a blackberry, a personal digital assistant (PDA), an ultra-mobile PC, a television, a video monitor, an audio system, or a similar device, for example.

The external device 140 may comprise a display 156.

The temperature monitoring apparatus 102 may comprise a communication port 160 for transmitting detected data or signals to the external device 140 and/or for receiving signals from the controller 124 and/or the external device 140. The transmission of the data from the temperature monitoring apparatus 102, via the communication port 160, may be controlled by the controller 124 or by any other controller, such as a controller 158, of the external device 140.

The communication port 160 may, for example, include a transmitter, a transponder, an antenna, a transducer, an RLC circuit, wireless and/or wired communication means. In some embodiments, the communication port 160 may comprise connection ports and interfaces such as a HDMI port, an A/V port, an optical cable port, a USB port and/or an AV connection port.

Communication between the temperature monitoring apparatus 102 and the external device 140 may be provided by any suitable communication module, which may include in a non-limiting example, wireless communication means, such as by cellular or WiFi communication, Cloud communication, Internet of things (IoT), Internet, Intranet, acoustic communication, Radio Frequency (RF), Bluetooth, Ultrasound communication, Light Transmission means, infrared or other wireless communication means. The communication module may comprise wired communication facilitated by any suitable means such as twisted pair, coaxial cable, cables, fiber optics, wave guides, Ethernet or USB or any other wired media.

The temperature sensors 110, 112 or 134 may comprise platinum resistors, thermistors, thermo-couples and/or transistors or any other suitable configuration for temperature sensing.

The temperature monitoring apparatus 102 may comprise electronic components and/or connectors 166 for electronic communication within the temperature sensor subassembly 106 and with the controller 124 and/or any other components of the temperature monitoring apparatus 102. The electronic components 166 may comprise any suitable components for detecting, processing, storing and/or transmitting data or signals, such as electrical circuitry, an analog-to-digital (A/D) converter, and an electrical circuit for analog or digital short or long-range communication, for example, as well as electronics for providing the components of the temperature monitoring apparatus 102 with power supply or electronic contacts between the various components of the temperature monitoring apparatus 102. In some embodiments, the data or signals may be stored in the Cloud, Internet of things (IoT), Internet and/or Intranet.

The temperature monitoring apparatus 102 may comprise logic components for the operation of the controller 124, such as comparators for comparing the detected temperatures by temperature sensors 110, 112 or 134, and/or adaptors and signal amplifiers, for example.

Some components of the temperature monitoring apparatus 102 may be positioned intermediate the housing 152 and the temperature sensor subassembly 106, such as the controller 124, memory 126, environmental sensor 134, bodily function sensor 142, power supply source 154 and communication port 160. At least some of these components may be embedded with the peripheral thermal insulation layer 150. The housing 152, peripheral thermal insulation layer 150 and the components embedded therein may be collectively referred to as the housing subassembly 168.

The heater 118 may be positioned latterly intermediate the first and second temperature sensors 110 and 112, as shown in FIGS. 1A & 1B. In some embodiments, the heater 118 may be positioned above the second temperature sensor 112, or below the first temperature sensor 110 or intermediate the first and second temperature sensors 110 and 112. In some embodiments, the heater 118 may be positioned longitudinally, alongside the first and second temperature sensors 110 and 112. In some embodiments, a plurality of heaters 118 may be provided at a various locations within the temperature monitoring apparatus 102 or may be spatially arranged within the temperature monitoring apparatus 102. In some embodiments, an additional heater 118 may be activated whereupon a first heater is dysfunctional.

As seen in FIG. 2, a portable temperature monitoring apparatus 102 may be placed on a user 170 and may be operative in the outdoors, remote from an electrical grid, for a relatively prolonged time period, such as a day or a few days, longer or shorter. The temperature monitoring apparatus 102 may be designed for efficient and minimal use of the power source 154, e.g. the battery, as operation of the measurement mode uses passive components, which require minimal or no power consumption, such as the first and second temperature sensors 110 and 112. Substantially, only during the calibration mode (e.g. an "active mode") are the active component or elements (e.g. the heater 114) activated. During the remaining operation of the temperature monitoring apparatus 102, such as when the apparatus is off or during the measurement mode (e.g. the "passive mode") the passive elements operate in the temperature monitoring apparatus 102.

FIGS. 3A and 3B are respective assembled and disassembled simplified, exemplary illustrations of the temperature monitoring apparatus 102. The temperature monitoring apparatus 102 may be positioned on the skin in any suitable manner, such as via an adhesive layer 180, or strap or band 184 (FIG. 4) and/or a combination thereof. The temperature monitoring apparatus 102 may comprise a reusable portion and a disposable portion. In some embodiments, the adhesive layer 180 may be disposable and the temperature monitoring apparatus 102 may be reusable. In some embodiments, as shown in FIGS. 3A and 3B, the disposable portion may comprise the adhesive layer 180 and the temperature sensor subassembly 106 and the reusable portion may comprise the housing subassembly 168.

In some embodiments, the temperature monitoring apparatus 102 may be secured to the user's apparel or a wearable band 184, such as a chest band or headband, as shown in FIG. 2.

Figure 4:
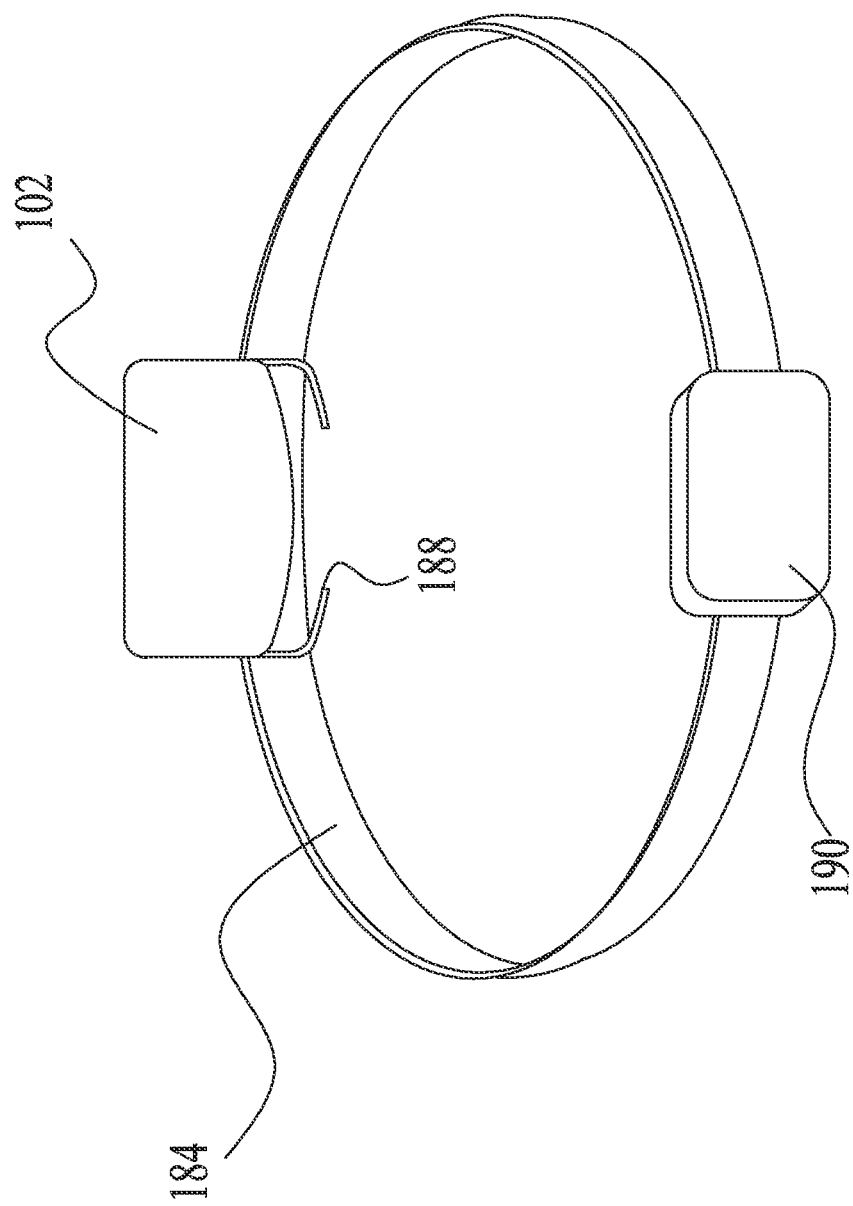
FIG. 4 is a simplified, exemplary illustration of a temperature monitoring apparatus constructed and operative according to some embodiments of the present disclosure.

Turning to FIG. 4 it is shown that the temperature monitoring apparatus 102 may be mechanically attached to a strap or the band 184 via a clasp 188 or any other suitable attachment means. The temperature monitoring apparatus 102 may be fixed to the band or may be removable therefrom.

In some embodiments, an EKG device or a heart rate monitor 190 or any other device configured for pulse detection, may be provided to verify physical coupling of the temperature monitoring apparatus 102 to the user's epidermis surface 104. The heart rate monitor 190 may be embedded within the band 184 or may be positioned in any suitable location.

In some embodiments, in a non-limiting example, the temperature monitoring apparatus 102 may be positioned on a sweatband, a hat, a helmet or on a wrist band or a watch.

Figure 5:
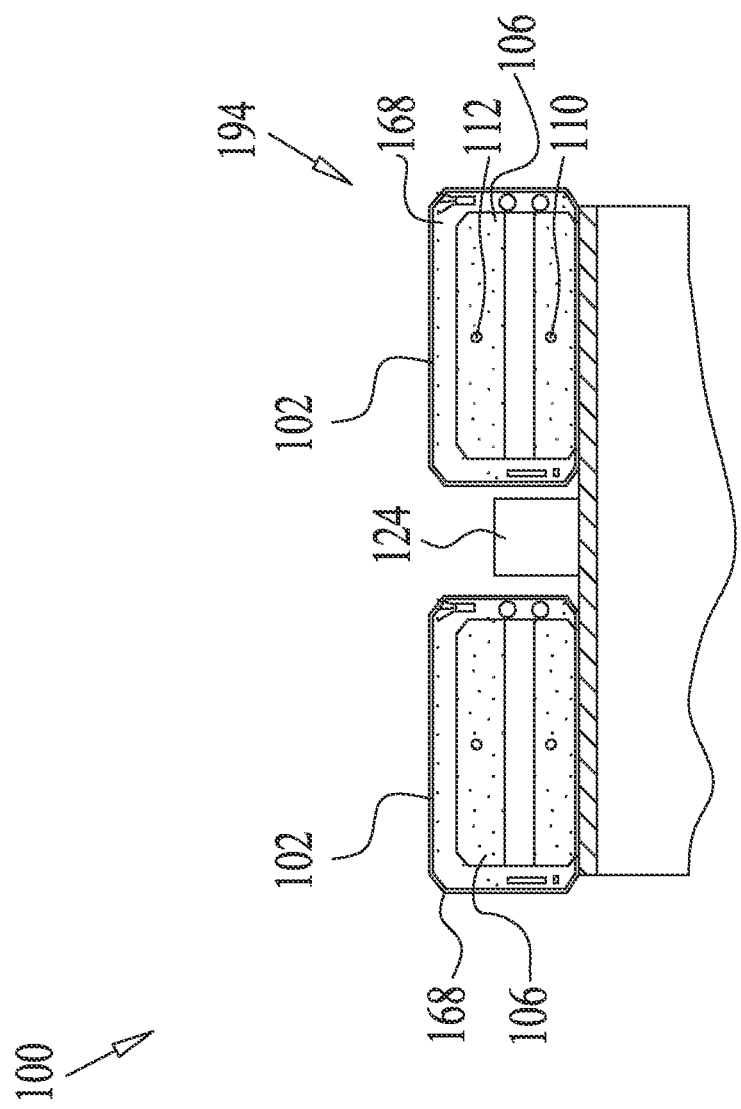
FIG. 5 is a simplified, exemplary illustration of a temperature monitoring apparatus constructed and operative according to some embodiments of the present disclosure.
Figure 6A:
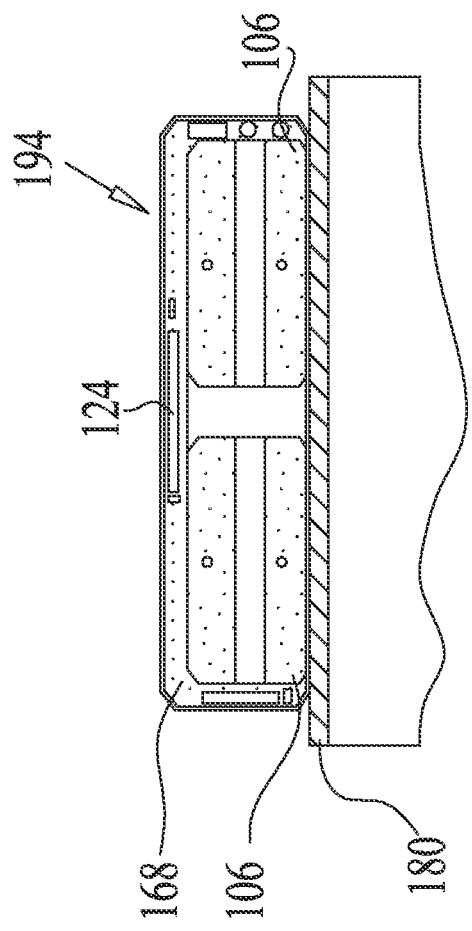
FIGS. 6A and 6B are respective assembled and disassembled simplified, exemplary illustrations of a temperature monitoring apparatus, constructed and operative according to some embodiments of the present disclosure.
Figure 6B:
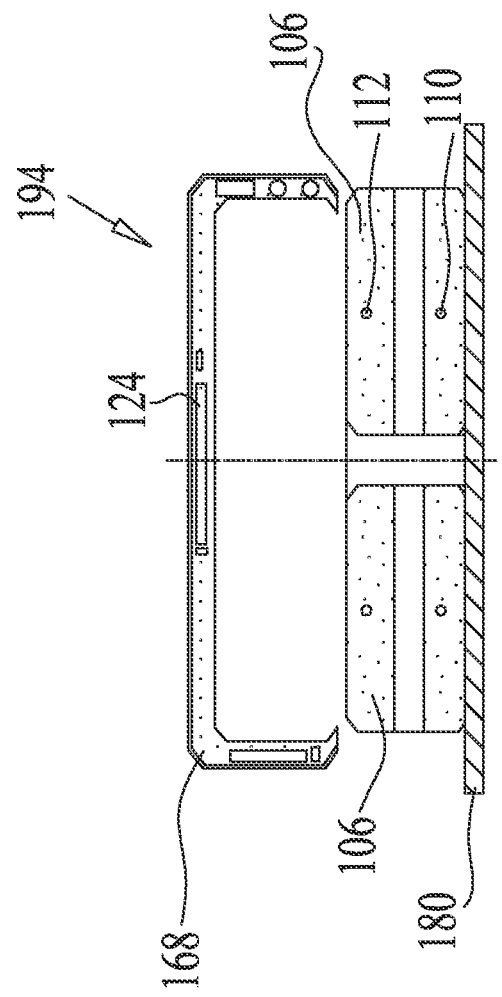

As seen in FIGS. 5, 6A and 6B, the temperature monitoring system 100 may comprise a plurality of temperature monitoring apparatuses 102 such that when a first temperature monitoring apparatus 102 is operating in a calibration mode, a second temperature monitoring apparatus 102 may operate in a measurement mode. A common controller 124 controls the operation of the first and second temperature monitoring apparatus 102. As seen in FIG. 5, the plurality of temperature monitoring apparatuses 102 may each comprise its own housing subassembly 168 and communication means with the common controller 124. In FIG. 2, the first and second temperature monitoring apparatuses 102 are shown placed on the user's forehead via band 184.

Turning to FIGS. 6A and 6B, a dual or multiple temperature monitoring apparatus 194 may be formed with a plurality of temperature sensor subassemblies 106 embedded in a single, common housing subassembly 168.

The multiple temperature monitoring apparatus 194 may be positioned on the skin in any suitable manner, such as via the adhesive layer 180 or band 184 (FIG. 4). In some embodiments, the multiple temperature monitoring apparatus 194 may comprise a reusable portion and a disposable portion. In some embodiments, the adhesive layer 180 may be disposable and the multiple temperature monitoring apparatus 194 may be reusable. In some embodiments, as shown in FIG. 6B, the disposable portion may comprise the adhesive layer 180 and the plurality of temperature sensor subassemblies 106 and the reusable portion may comprise the housing subassembly 168. In some embodiments, the reusable portion may comprise the plurality of temperature sensor subassemblies 106 and the disposable portion may comprise the housing subassembly 168.

In some embodiments, upon detection of inoperativeness of a first temperature monitoring apparatus 102 or of decoupling of the first temperature monitoring apparatus 102 from the skin, the second temperature monitoring apparatus 102 may replace the first temperature monitoring apparatus 102.

FIG. 7 is a simplified flowchart of a method for determining the core body temperature using the temperature monitoring system 100. At a first optional step 200 the controller 124 verifies proper coupling of the temperature monitoring apparatus 102 to the epidermal surface 104 (i.e. skin), such as by detecting the user's pulse in association with the temperature monitoring apparatus 102. At step 204 the initial calibration mode is activated to determine a physical property of the subdermal tissue. In some embodiments the physical property is the thermal conductivity constant of the subdermal tissue, $C_t$.

To calculate $C_t$, in some embodiments, at step 206 a ZHF phase is activated by the heater 118 to generate an isothermal channel, extending longitudinally through the temperature sensor subassembly 106 from the second temperature sensor 112 to the first temperature sensor 110 through to the subskin location 120. As temperature equilibrium is achieved, the subskin tissue temperature, $T_{0t}$ is established as equaling $T_1$ (and $T_2$, as well). $T_{0t}$ is the subdermal temperature measured at subskin location 120 during the ZHF mode and may comprise a calibration, instantaneous subdermal temperature measurement.

The controller 124 terminates the heater operation thereby commencing a HF phase at step 208 by creating a heat flow channel, such that $T_1$ is larger or smaller than $T_2$, and $T_1 \neq T_2$. The stored $T_{0t}$ may be retrieved for calculating $C_t$, according to the Heat Flux formulation, as described herein, such that $$Ct = \frac{(T1 - T2)C1}{T0t - T1}$$

At step 210 the measurement mode is activated and the detected temperatures $T_1$ and $T_2$ of the respective first and second temperature sensors 110 and 112 are transmitted to the controller 124. Based on $T_1$, $T_2$, the predetermined thermal conductivity constant of the insulation layer 114 $C_1$, and the retrieved calculated $C_t$, the subdermal tissue temperature $T_0$ may be calculated by Equation 1, thereby determining the core body temperature $T_0$ $_{CBT}$, by proxy, in accordance with:

$$T_{0CBT} = T_0 = T_1 + \frac{(T1 - T2)C1}{Ct}$$

The controller 124 may be programmed with processor instructions for causing the switch 132 to alternate between the calibration mode and the measurement mode based on a predetermined change, as seen in step 214. This predetermined change may comprise one or a combination of at least any of the following conditions or triggers, such as a predetermined duration from a previous core body measurement. In a non-limiting example, the controller 124 may reactivate the calibration mode at 5, 10, 15, 30, 60 minutes or more intervals.

In some embodiments the change or trigger may comprise a change in an environmental condition, such as a change in the ambient temperature or humidity level. In a non-limiting example, once a change in a predetermined ambient temperature gradient is detected, e.g. 1° C., or 2° C., or 3° C., or 4° C. or 5° C. or more, the controller 124 activates the calibration mode. In another non-limiting example, once a predetermined ambient temperature threshold is detected, e.g. 32° C. or more the controller 124 activates the calibration mode.

In some embodiments, the change may comprise a rate of the temperature change. For example, a 1° C. rise within a duration of 10 minutes may trigger activation of the calibration mode, while when a 1° C. rise within a duration of 2 hours is detected, the calibration mode is not activated.

In some embodiments, the change may comprise a change in the measure of sun radiation. The sun radiation may be measured by any suitable radiation meter and may be indicative of high risk for heat stress. Heat stress can result in heat-related illnesses, such as heat stroke, hyperthermia, heat exhaustion, heat cramps or heat rashes and even death.

In some embodiments, the change may comprise a change in a plurality of parameters indicating heat stress, such as sun radiation level, ambient temperature, humidity level, air movement, etc.

In some embodiments the change may comprise a change in a physical condition of the user, such as skin temperature, cardiac activity, physical activity levels, changes in dermal blood perfusion, changes in perspiration levels secreted from the user. In a non-limiting example, once a predetermined skin temperature threshold is detected, e.g. 35° C., the controller 124 activates the calibration mode.

In some embodiments, the switch 132 may be activated by the user 170, e.g. manually, for alternating between the calibration mode and the measurement mode.

Where the change is identified at step 214 the switch 132 is triggered to activate the calibration mode of step 204. If the change has yet to occur, the system 100 remains in the measurement mode of step 210. Thus the core body temperature may be continuously and accurately determined and monitored.

In some embodiments, the operation of the temperature monitoring system 100 may be performed via an application operating on the external device 140 (FIG. 1A) and communicated to the user 170 via the display 156.

In some embodiments, as described in reference to FIGS. 1A-2, it can be assumed that the tissue temperature $T_0$ is substantially similar to the core body temperature $T_0$ $_{CBT}$.

The local blood perfusion rate may be indicative of the congruousness and similarity of the subdermal tissue temperature $T_0$ with the core body temperature $T_0$ $_{CBT}$. A greater local blood perfusion rate is indicative of increased congruousness of the subdermal tissue temperature $T_0$ with the core body temperature $T_0$ $_{CBT}$.

In some embodiments, a difference between the $T_0$ and $T_0$ $_{CBT}$ may be present and may be estimated by the detected local blood perfusion rate. The controller 124 may be programmed to consider the degree of difference between the $T_0$ and $T_0$ $_{CBT}$, such as by including a correction factor, for example.

The dermal blood perfusion rate may be measured in any suitable manner, such as by an optical device or an acoustical device as described herein. In some embodiments, the temperature sensor subassembly 106 may be used to measure the dermal blood perfusion rate by detecting the amount of time it takes for the subskin temperature $T_{0t}$ to return to its initial temperature following heating by the heater 118 (generally during the calibration mode). During heating at ZHF mode, the subskin temperature $T_{0t}$ is equal to $T_1$, as described herein. Accordingly, $T_1$ can indicate the subskin temperature $T_{0t}$.

FIG. 8 is a simplified flowchart of a method for determining the core body temperature using the temperature monitoring system 100. Following the optional verification step 200 (FIG. 7) and the initial calibration steps 204, 206 and 208, the measurement mode 210 may be activated until a change is detected. In some embodiments this change or trigger may comprise the physical state of the user, namely is the user active or at rest, as shown in step 250. When an active state is detected an active recalibration mode may be operated, as shown in step 252. The active recalibration mode may comprise a relatively short recalibration cycle wherein the recalibration is initiated at relatively short intervals, e.g. every 20 minutes. When a rest state is detected a rest recalibration mode may be operated, as shown in step 254. The rest recalibration mode may comprise a relatively long recalibration cycle wherein the recalibration is initiated at relatively long intervals, e.g. every 1 or 2 hours. At predetermined time periods the calibration inquires the physical state of the user at step 250.

According to an embodiment of the present disclosure the determined core body temperature may be compared to a safety threshold temperature by the controller 124 or by the external device 140. When the core body temperature reaches the safety threshold temperature, precautions may be taken to prevent the user 170 from slipping into hyperthermia or hypothermia.

In some embodiments the safety threshold temperature may be a predetermined global value used for a large population. For example, the safety threshold temperature may be predetermined to be 38° C. Whereupon the core body temperature is detected as 38° C., the user 170 or others may be alerted by the external device 140 or by any other means to cool down. In some embodiments the safety threshold temperature may be determined according to the user's previous history which may be stored in the external device 140.

The bodily subdermal temperature may be determined based on Heat Flux formulations. The Heat Flux formulations may comprise Equation (1) described herein. In some embodiments the Heat Flux formulation may be based on Equation (2):

$$T_0 = T_1 + \frac{(T_1 - T_2)C_1}{C_t} + \frac{C_{insu} \cdot A_{surf}}{C_1 \cdot A_{med}} \cdot \left(\frac{T_1 + T_2}{2} - T_{surf}\right).$$ Equation (2)

In Equation (2) the subdermal temperature $T_0$ is calculated based on Equation (1) whilst escaped heat due to imperfect insulation is considered as well. In some instances, the intermediate and/or peripheral thermal insulation layers 114 and 150 may be imperfect, and thus heat flows towards the outer surface of the housing 152. The temperature at the housing surface is denoted by $T_{surf}$. The temperature difference between the intermediate thermal insulation layer 114 separating the first and second temperature sensors 110, 112 and the housing 152 may be written as:

$$(T_1 + T_2)/2 - T_{surf}$$

This temperature difference is compounded by the product of the thermal conductivity constant of the peripheral thermal insulation layer 150, denoted by $C_{insu}$ and the surface area thereof, denoted by $A_{surf}$ and by the product of the intermediate thermal insulation layer 114 thermal conductivity constant $C_1$, and the surface area thereof, denoted by $A_{med}$.

Such that:

$$\frac{C_{insu} \cdot A_{surf}}{C_1 \cdot A_{med}} \cdot \left(\frac{T_1 + T_2}{2} - T_{surf}\right)$$

Hence Equation (2) is formulated.

The parameters $C_{insu}$, $A_{med}$, $A_{surf}$ are predetermined by the design of the temperature monitoring apparatus 102. $T_{surf}$ may be measured directly using a temperature sensor positioned on the surface of the housing 152.

In some embodiments, the $T_{surf}$ may be calculated based on the Heat Flux formulations, such that:

$$T_{surf} = \frac{C_{out} \cdot T_2 + C_{insu}\left(\frac{T_1 + T_2}{2}\right) - C_t(T_1 - T_2)}{C_{out} + C_{insu}}$$

While $C_{out}$ is the heat conductivity constant from the housing 152 outer surface to the ambient.

$C_{out}$ may depends on ambient conditions such as the air temperature, air flow speed and humidity, which can be measured by environmental sensors 134.

In some embodiments additional terms can be added to Equation 1 or Equation 2 to improve accuracy and/or compensate for additional factors that influence the measurement. In some embodiments, calibration parameters, such as $C_t$ or $C_1$ can be obtained from operating the heater 118 for a shorter period even without getting to ZHF condition, for instance by estimating the temperature $T_1$ and/or $T_2$ change rates. In some embodiments, calibration parameters, such as $C_t$ or $C_1$ can be obtained from additional sources, such as additional sensors.

Figure 9:
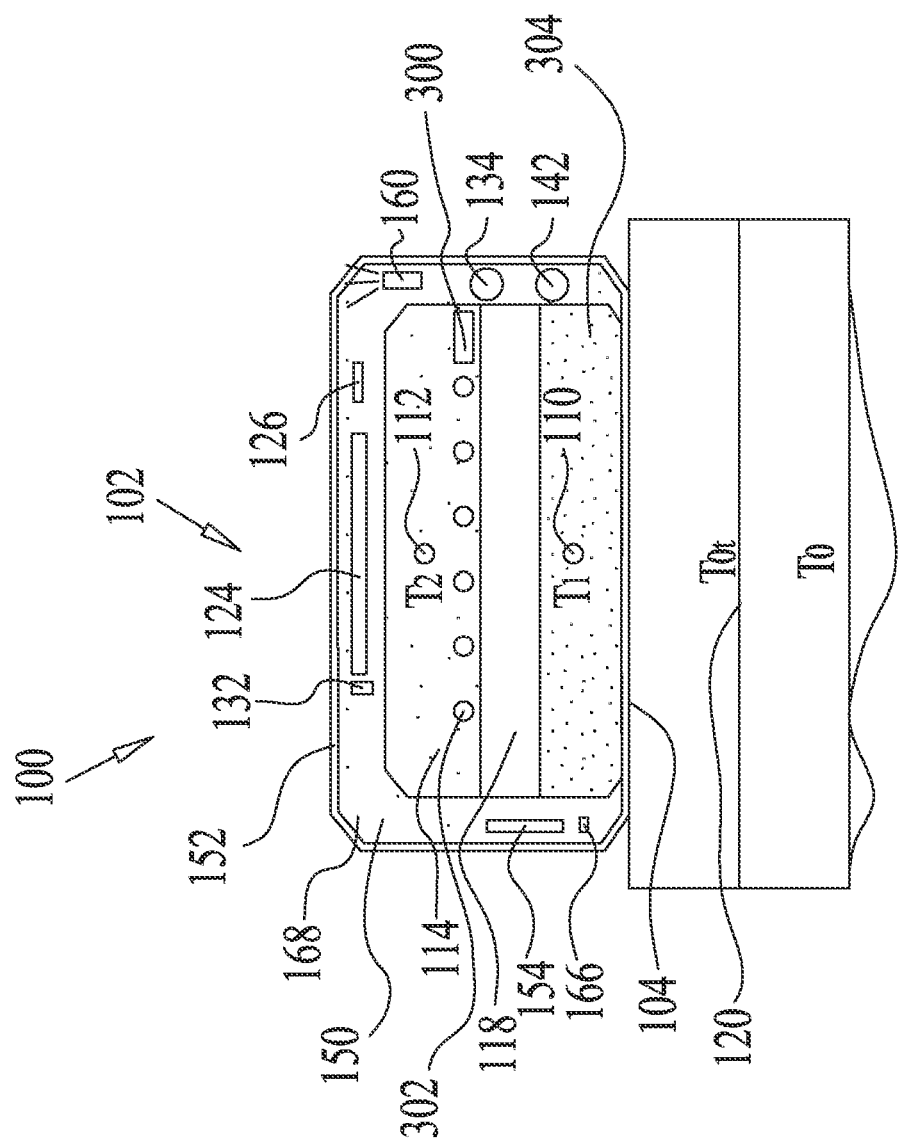
FIG. 9 is a simplified, exemplary illustration of a temperature monitoring apparatus constructed and operative according to some embodiments of the present disclosure.

As seen in FIG. 9, in some embodiments, a heat flux sensor 300 can be operated at so called "partial zero heat flux" i.e. the heat flux sensor includes a heater as in the zero heat flux sensor, however to save battery energy and to obtain faster calibration, the heater is not operated long enough to get to zero heat flux conditions, but just partially heats to induce external heat for estimating the calibration parameters (e.g. $C_t$) as well as the core body temperature.

In some embodiments, the temperature monitoring apparatus 102 may include additional temperature sensors 302 located in between the first and second temperature sensors 110 and 112 or anywhere else such as spatially arranged at any suitable location, to further improve the temperature estimation.

In some embodiments, the temperature monitoring apparatus 102 may include at least one additional thermal insulation layer 304 with thermal properties (e.g. thermal conductivity, thermal capacitance) which may be the same or different from the thermal insulation layer 114 and additional temperature sensors 302 located in between the additional thermal insulation layer and the thermal insulation layer 114 to further improve the temperature estimation.

In some embodiments, additional terms can be added to Equation 1 or Equation 2 to improve accuracy and/or compensate for additional factors that influence the measurement or other equations which describes the thermal dynamics. For instance, other additional factors which can be included are the spatial temperature distribution in the subskin location 120 itself and in the whole volume around the subskin location 120 including the tissue and the area in the vicinity of the subskin location 120. For instance, the temperature, as well as the thermal properties at the different layers of tissue below the temperature monitoring apparatus 102, can be estimated from the thermal dynamics. In some embodiments, the thermal dynamics can be modeled by diffusion equations over finite elements model, in which local thermal properties as well as their temporal dynamics can be estimated during the temperature monitoring apparatus 102 operation to further improve accuracy.

It is noted that the temperature monitoring apparatus 102 may comprise a device or system or portions of a system. The controller 124 may comprise a control unit or control element.

Various implementations of some of embodiments disclosed, in particular at least some of the processes discussed (or portions thereof), may be realized in digital electronic circuitry, integrated circuitry, specially configured ASICs (application specific integrated circuits), computer hardware, firmware, software, and/or combinations thereof. These various implementations, such as associated with the system 100 the components thereof, for example, may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

Such computer programs (also known as programs, software, software applications or code) include machine instructions/code for a programmable processor, for example, and may be implemented in a high-level procedural and/or object-oriented programming language, and/or in assembly/machine language. As used herein, the term "machine-readable medium" refers to any computer program product, apparatus and/or device (e.g., non-transitory mediums including, for example, magnetic discs, optical disks, flash memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein may be implemented on a computer having a display device (e.g., a LCD (liquid crystal display) monitor and the like) for displaying information to the user and a keyboard and/or a pointing device (e.g., a mouse or a trackball, touchscreen) by which the user may provide input to the computer. For example, this program can be stored, executed and operated by the dispensing unit, remote control, PC, laptop, smartphone, media player or personal data assistant ("PDA"). Other kinds of devices may be used to provide for interaction with a user as well. For example, feedback provided to the user may be any form of sensory feedback (e.g., visual feedback, auditory feedback, or tactile feedback), and input from the user may be received in any form, including acoustic, speech, or tactile input. Certain embodiments of the subject matter described herein may be implemented in a computing system and/or devices that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components.

The components of the system may be interconnected by any form or medium of digital data communication (e.g., a communication network). Examples of communication networks include a local area network ("LAN"), a wide area network ("WAN"), and the Internet. The computing system according to some such embodiments described above may include clients and servers. A client and server are generally remote from each other and typically interact through a communication network. The relationship of client and server arises by virtue of computer programs running on the respective computers and having a client-server relation to each other.

Any and all references to publications or other documents, including but not limited to, patents, patent applications, articles, webpages, books, etc., presented anywhere in the present application, are herein incorporated by reference in their entirety.

Example embodiments of the devices, systems and methods have been described herein. As may be noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, systems and devices which may further include any and all elements/features from any other disclosed methods, systems, and devices, including any and all features corresponding to translocation control. In other words, features from one and/or another disclosed embodiment may be interchangeable with features from other disclosed embodiments, which, in turn, correspond to yet other embodiments. Furthermore, one or more features/elements of disclosed embodiments may be removed and still result in patentable subject matter (and thus, resulting in yet more embodiments of the subject disclosure).

The invention claimed is:

1. A core body temperature monitoring apparatus configured to be placed superdermally over a user's skin, comprising:
   a passive element;
   an active element; and
   a controller comprising a switch, the switch configured for alternating between:
      an active mode wherein the active element is activated for calculating a subdermal tissue thermal conductivity constant; and
      a passive mode, wherein the active element is terminated and the core body temperature is determined, based on signals received by the passive elements and the calculated subdermal tissue thermal conductivity constant.

2. An apparatus according to claim 1 wherein the passive elements comprise:
   a first temperature sensor;
   a second temperature sensor;
   a thermal insulation layer positioned intermediate the first and second temperature sensors; and
   wherein the active element comprises a heater for heating the apparatus and a subdermal tissue region underlying the user's skin.

3. An apparatus according to claim 2, wherein the heater is positioned intermediate the first temperature sensor and the second temperature sensor.

4. An apparatus according to claim 3, wherein the heater is positioned within the thermal insulation layer.

5. An apparatus according to claim 3, further comprising at least one additional heater.

6. An apparatus according to claim 5, wherein the additional heater is positioned at least at one of the following positions: (i) intermediate the first temperature sensor and the second temperature sensor, (ii) below the first temperature sensor and (iii) above the second temperature sensor.

7. An apparatus according to claim 1, further comprising a housing and a peripheral thermal insulation layer.

8. An apparatus according to claim 1, wherein the controller is embedded within a peripheral thermal insulation layer.

9. An apparatus according to claim 1, wherein a EKG device is provided to verify physical coupling of the apparatus to the user's epidermis surface.

10. An apparatus according to claim 1, further comprising at least one of an ECG, a pulse meter, a pedometer and an optical Doppler sensor.

11. An apparatus according to claim 1, wherein the controller has operating thereon processor instructions for causing the switch to alternate between the active mode and the passive mode based on at least one of:

a predetermined duration from a previous core body measurement;

a change in an environmental condition; and a change in a physical condition of the user.

12. An apparatus according to claim 2, wherein:

the first temperature sensor is configured to measure a temperature $T_1$, the second temperature sensor is configured to measure a temperature $T_2$, and the thermal insulation layer is designed with a thermal conductivity constant $C_1$, the heater is operative to be heated until temperature equilibrium is achieved between the first temperature sensor and the second temperature sensor;

the first or second temperature sensor are operative to establish a subskin tissue temperature, $T_{0t}$;

the thermal conductivity constant of the subdermal tissue, is calculated according to:

$$Ct = \frac{(T1-T2)C1}{T0t-T1}.$$

\* \* \* \* \*